United States Patent [19]

Horowitz et al.

[11] Patent Number: 5,232,748
[45] Date of Patent: Aug. 3, 1993

[54] METHOD OF GRAFTING POLYMERIZABLE MONOMERS ONTO SUBSTRATES

[75] Inventors: Carl Horowitz, Brooklyn; Paulose Thottathil, New Hyde Park; Mohan Sanduja, Flushing, all of N.Y.

[73] Assignee: Polymer Research Corp. of America, Brooklyn, N.Y.

[21] Appl. No.: 780,102

[22] Filed: Oct. 21, 1991

[51] Int. Cl.$^5$ ............................................. B05D 3/06
[52] U.S. Cl. .................................... 427/553; 427/302; 427/303; 427/399; 427/554; 427/322
[58] Field of Search ............... 427/451, 554, 553, 302, 427/303, 322, 399

[56] References Cited

U.S. PATENT DOCUMENTS 3,401,049 9/1968 Horowitz .............................. 427/302
4,960,611 10/1990 Fujisawa et al. ............... 427/45.1 X
5,137,758 8/1992 Kistner et al. ....................... 427/350

Primary Examiner—Michael Lusigan
Attorney, Agent, or Firm—Steinberg & Raskin

[57] ABSTRACT

The invention relates to the chemical bonding of a polymer or polymers onto a non-metallic substrate such as cellophane by contacting the substrate with a silver nitrate solution followed by treatment with an alkali hydroxide such as sodium hydroxide or potassium hydroxide, whereby particles of silver or silver oxide are uniformly distributed in situ throughout the surface of the substrate, contacting the thus treated substrate with a grafting solution that contains monomers, prepolymers, catalysts and possibly other ingredients, to obtain graft polymerization onto the substrate with intimate bonding of the polymer onto the substrate surface, and curing the polymer on the substrate by microwave or laser energy.

9 Claims, No Drawings

METHOD OF GRAFTING POLYMERIZABLE MONOMERS ONTO SUBSTRATES

BACKGROUND OF THE INVENTION

Polymers have been grafted onto non-metallic substrate surfaces, such as cellophane, for example, as described in U.S. Pat. No. 3,401,049. The basic process of grafting of the polymer comprises the contacting of the non-metallic body, for example, with a solution of silver nitrate and an alkali metal hydroxide, then contacting the thus treated body with a polymerizable composition of a polymerizable monomer and a catalyst, the polymerization taking place directly on the molecules of the substrate. As described in U.S. Pat. No. 3,401,049, the polymerization can take place at room temperature, in which case, considerable time is required, or it can be accelerated by heat.

In more recent processing, the grafting of the polymer onto the substrate has utilized radiation, corona discharge, UV treatment and thermal treatment to accelerate the polymerization and cure the polymer. The processing is in general the same, namely the activated surface of the substrate is brought into contact with a grafting solution which contains the monomers, prepolymers, catalyst and graft initiator system, and the resulting graft treated surface is then subjected to cure as set forth above.

However, all of the methods are either too hazardous, such as grafting by means of radiation, or too time and energy consuming, such as grafting by UV or thermal treatment.

The need has arisen for a more rapid yet safe method of grafting of polymers onto substrates.

SUMMARY OF THE INVENTION

Generally speaking in accordance with the present invention, polymers are grafted onto substrates by distributing particles of silver or silver oxide in situ onto the surface of the substrate in such manner that silver particles are bonded to the surface, bringing the thus treated substrate surface into contact with a polymerizable composition of a monomer or prepolymer and a polymerization activator, such as a catalyst, and subjecting the same to microwaves or laser energy to accelerate the polymerization and cause grafting of the resulting polymer onto the surface of the substrate.

It is accordingly a primary object of the present invention to provide methods of accelerating the polymerization of polymerizable monomers or prepolymers onto non-metallic substrates, such as cellophane.

It is yet a further object of the present invention to accelerate the polymerization onto treated substrates by microwave or laser energy.

Other objects and advantages of the present invention will be apparent from a further reading of the specification and of the appended claims.

The present invention is applicable to grafting of polymers onto a wide variety of non-metallic materials such as cellophane, cotton fibers and fabrics, rayon fibers and fabrics, wood, nylon fibers, fabrics and films, fibers, fabrics, and other films, polyethylene glycol adipate films, cellulose triacetate fibers, fabrics and films, polyolefine fibers and fabrics, natural and synthetic rubbers, leather, wool, hair, animal and human skin, bone, teeth, body tissues, glass, paper and many others.

For purposes of simplicity, the invention will be in general be described with respect to the treatment of cellophane as the substrate.

The invention is applicable to the use of any polymerizable monomer or prepolymer such as: vinylidene chloride, chloroprene, isoprene, dimethylaminoethyl methacrylate, styrene, 1,3-butylene dimethacrylate, hydroxyethyl methacrylate, isoctylvinyl ether, acrylonitrile, acrylamide, N-vinyl pyridine, glycidyl methacrylate, N-vinyl caprolactam, N-vinyl pyrrolidone, N-vinyl carbazole, acrylic acid, methacrylic acid, ethyl acrylate, ethyl methacrylate, itaconic acid, isobutylmethacrylate, methyl acrylate, sodium styrene sulfonate, sodium vinyl sulfonate, bis (beta-chloroethyl) vinyl phosphate, cetyl vinyl ether, divinylether of ethylene glycol, divinyl ether of butanediol, vinyl toluene, vinyl acetate, octadecyl vinylether. Also amines can be quaternized with benzyl chloride, ethyl iodide, methyl or ethylsulfate. Conversely, monomeric chlorides can be quaternized with tertiary amines to give quaternary ammonium compounds. Some suitable tertiary amines are: n-ethyl morpholine, pyridine, cetyldimethyl pyridine, methylmethacrylate.

According to the general method of grafting a polymerizable monomer onto a cellophane sheet, a uniform dispersion and distribution of particles of silver or silver oxide are formed in situ onto the surface of the cellophane film and the thus treated film is contacted with the polymerizable composition of the monomer, prepolymer catalyst and other ingredients of the composition, which is adapted to be activated to polymerization by the metallic silver and silver oxide whereby polymerization is caused and the resulting polymer is chemically bonded to the surface of the substrate.

The silver or silver oxide which is formed in situ on the cellophane sheet is obtained from a solution of silver nitrate which by the action of an alkali metal hydroxide precipitates the silver oxide or colloidal silver from the solution. The concentration of the silver nitrate in the initial silver nitrate solution can vary within wide ranges, although it is preferably between about 0.01% to 1% and most preferably between about 0.05% to 0.1%.

The alkali metal hydroxide is most preferably, from the point of view of economy and ready availability, sodium hydroxide, although other alkali metal hydroxides such as potassium hydroxide and lithium hydroxide can be used with equal facility. The concentration of the alkali metal hydroxide in the aqueous solution, assuming use of an aqueous solution, can vary within any range, although for practical convenience, the range is generally between about 0.5% and 5% by weight.

The monomer can be dissolved in a suitable solvent such as dimethylformanide, tetrahydrofurane, tetrahydrofurfuryl alcohol, dimethylsulfoxide, water, methyl, ethyl or isopropyl alcohol, acetone, methyl ethyl ketone and ethyl acetate. Also mixtures of two or more of the above can be used.

Among the catalysts which can be used are: ammonium persulfate, hydrogen peroxide, tert-butylhydroperoxide, ditert-butyl peroxide, benzoyl peroxide, dicumyl peroxide, lauroyl peroxide, tert-butyl perbenzoate and peracetic acid.

A combination of two or more monomers mentioned above can be grafted to obtain graft copolymers.

The concentration of the monomer in the solution can vary within practically any limits, for example, from between about 0.1% to 50%. However, the preferred concentration for facility of use is between about 5% and 15% by weight of the solution.

In the case of acceleration of the polymerization by microwave treatment, the treatment time is between about 2-5 minutes.

In the case of the use of laser energy to accelerate the graph polymerization, the time of treatment is shortened to less than one second up to about 30 seconds and possibly up to one minute.

Thus, the overall method of the present invention comprises activating the surface of a cellophane sheet or film by treatment with an aqueous silver nitrate solution followed by treatment in a solution of an alkali metal hydroxide. This preactivation can be accomplished, for example, by immersing the cellophane film in a reaction mixture obtained by the addition of alkali metal hydroxide to an aqueous silver nitrate solution, the alkali metal hydroxide being added in an amount just sufficient to achieve a permanent slight cloudiness. The pretreated cellophane surface is then treated by dipping into a monomer-catalyst solution. This is followed by curing of the treated film in a microwave for about 2-5 minutes, or by laser energy for as little as a part of a second up to one minute.

DESCRIPTION OF PREFERRED EMBODIMENTS

The following examples are given to further illustrate the invention. The scope of the invention is not, however, meant to be limited to the specific details of the examples.

The following is a general description of the method:

Graft coating compositions are prepared and each one is applied onto pre-activated cellophane film by dipping. The resulting monomer treated cellophane film is subjected to curing in a microwave oven for 2-5 minutes or by laser energy for up to one minute. The grafted cellophane film which is thus prepared is tested by adhesion, percent add-on, leaching with plain water and other characteristics. Before treating the cellophane with the monomer solution, the substrate is activated with graft activating solution, rinsed with water and air dried.

The following are the steps involved in the grafting of cellophane film:

I. Pretreatment Step—Treatment of Cellophane Film with Graft Activating Solution The steps involved in the treatment of cellophane film with graft activating solution are as follows:
1. Wash with water at ambient temperature for one minute.
2. Dip in 1% silver nitrate solution at room temperature for one minute.
3. Rinse in water at room temperature for 10-15 seconds.
4. Dip in 1% potassium hydroxide solution maintained at 80° C. for one minute.
5. Wash in water.
6. Subject to air dry.

II. Preparation of Monomer Solution—Grafting Solution.

Into 100 ml of water in a container are added the following ingredients:
dimethyl formamide
monomer mixture
ammonium persulfate
sodium metabisulfite The contents are stirred to a uniform solution.

III. Grafting of Monomer Solution onto Cellophane Film

A 8×11" cellophane sheet was pretreated with graft activating solution in accordance with the steps indicated in (I) above. The dry pretreated film was washed with water and then dipped into monomer solution prepared in (II) above. The monomer treated cellophane film was air dried for few minutes and the subjected to cure in a microwave oven for 2-5 minutes or by laser for 30 seconds. The grafted cellophane films thus prepared were then tested for various characteristics.

EXAMPLE I

I. Preactivating Solution

Solution A—wash with plain water at room temperature for one minute.

Solution B—dip in 1% silver nitrate solution at room temperature for one minute.

Solution C—rinse in water at room temperature for 10 seconds.

Solution D—dip in 1% potassium hydroxide solution at 80° CC for one minute.

Solution E—wash in plain water and dry.

II. Grafting Solution

|  | Parts by Weight |
| --- | --- |
| Water | 100.00 |
| Dimethylformanide (DMP) | 20.00 |
| Hydroxyethylmethacrylate | 8.00 |
| Acrylonitrile | 2.00 |
| Ammonium persulfate | 1.00 |
| Sodium metabisulfite | 1.00 |

Preactivated cellophane sheet was dipped in this solution, air dried and subjected to cure in a microwave for 5 minutes or by laser for 45 seconds.

The grafted cellophane which was clear and transparent, increased in weight to 20.58%. The cellophane sheet which was not preactivated but treated with grafting solution and cured in a microwave, exhibited an increase in weight to 2.63%.

EXAMPLE II

I. Preactivating solution is the same as in Example I.

II. Grafting Solution

|  | Parts by Weight |
| --- | --- |
| Water | 100.00 |
| Dimethyl formamide | 20.00 |
| Acrylonitrile | 2.00 |
| 2-acrylamido 2 methylpropane sulfonic acid (AMPS) | 8.00 |
| Ammonium persulfate | 1.00 |
| Sodium metabisulfite | 1.00 |

The cellophane sheet grafted in accordance with procedures of Example I was clear and transparent and indicated an increase in weight to 19.76%. However, non-activated cellophane but treated with grafting solution and cured in a microwave or by laser exhibited an increase in weight to 300%.

EXAMPLE III

I. Preactivating solution is the same as in Example I.

II. Grafting Solution

|  | Parts by Weight |
| --- | --- |
| Water | 150.00 |
| Dimethylformamide (DMF) | 30.00 |
| 2-acrylamide-2-methylpropane sulfonic acid (AMPS) | 12.00 |
| Hydroxy ethyl methacrylate | 3.00 |
| Ammonium persulfate | 1.50 |
| Sodium metabisulfite | 1.50 |

The grafted cellophane sheet exhibited an increase in weight to 20.78%. However, non-activated cellophane sheet treated with grafting solution and cured by microwave or laser, showed an increase in weight to 2.46%.

EXAMPLE IV

I. Preactivating solution is the same as in Example I.

II. Grafting Solution

|  | Parts by Weight |
| --- | --- |
| Water | 100.00 |
| Dimethylformamide | 20.00 |
| Sodium styrene sulfonate | 8.00 |
| Glacial acetic acid | 1.00 |
| Glycidyl methacrylate | 2.00 |
| Ammonium persulfate | 1.00 |

The cellophane sheet grafted in accordance with the procedure of Example I, exhibited an increase in weight to 21.01%. However, non-activated cellophane sheet treated with grafting solution and cured in a microwave or by laser showed an increase in weight to 2.76%.

Testing of Grafted Cellophane Sheet—Adhesion and Percent Add on (Increase in Weight)

1. Adhesion

A piece of Scotch Brand Cellophane was implanted firmly against a grafted cellophane film and then pulled upward sharply. No visual delamination of the grafted polymer film from base material cellophane sheet was observed. This indicated that grafting of polymerizable monomer to a polymer onto cellophane sheet was strongly bonded chemically.

2. Percent Add On—Increase in Weight of Grafted Cellophane Sheet

The grafted cellophane sheet was estimated for increase in weight with respect to control (non-grafted cellophane sheet). The increase in weight in each case is given in Table I.

TABLE I

| | Increase in weight of grafted and non-grafted cellophane sheet. | |
| --- | --- | --- |
| Examples | Increase in Weight Grafted Cellophane Sheet (0/0) | Increase in weight non-Grafted Cellophane Sheet (0/0) |
| I | 20.58 | 2.63 |
| II | 19.76 | 3.00 |
| III | 20.78 | 2.46 |

TABLE I-continued

| | Increase in weight of grafted and non-grafted cellophane sheet. | |
| --- | --- | --- |
| Examples | Increase in Weight Grafted Cellophane Sheet (0/0) | Increase in weight non-Grafted Cellophane Sheet (0/0) |
| IV | 21.01 | 2.76 |

In order to test the durability of increase in weight to grafted cellophane sheet, the grafted cellophane sheet obtained in each example was washed with plain water for 5 minutes at room temperature, air dried and weighed again. The washings were also carried out in case of non-grafted cellophane sheet (control). The results are summarized in Table II.

TABLE II

| | Weight of Grafted and Non-Grafted Cellophane Sheet After Washings With Plain Water At Room Temperature | |
| --- | --- | --- |
| Examples | Weight after Washing Grafted Cellophane Sheet (0/0) | Weight after Washing Grafted Cellophane Sheet (0/0) (Control) |
| I | 20.58 | 0.03 |
| II | 19.76 | 0.12 |
| III | 20.78 | 0.08 |
| IV | 20.89 | 0.00 |

As can be seen from the results in Table II, there is no significant loss in weight of grafted cellophane sheet after washings thereby indicating that the attachment of polymer to the surface of the cellophane sheet is permanent. However, in case of the non-grafted cellophane sheet (control), there is a significant loss in weight after washings. This indicated that the attachment of polymer to non-grafted cellophane film (control) was physical rather than chemical.

What is claimed is:

1. In a method of grafting a polymer onto a non-metallic substrate which comprises activating the substrate by contacting the same with a solution of silver nitrate and precipitating silver oxide or colloidal silver therefrom by means of an alkali hydroxide, contacting the thus activated substrate with a polymerizable composition including a catalyst and being adapted to be activated to polymerization by the silver oxide or colloidal silver so as to cause polymerization at sites thereof on the substance to bind the resulting polymer directly to the substrate, and curing the resulting polymer to effect intimate binding there to the substrate, the improvement which comprises effecting the curing by application of microwave or laser energy.

2. The method of claim 1 wherein the curing is effecting by microwave energy applied for a time period of 2-5 minutes.

3. Method according to claim 1 wherein the curing is effecting by laser energy applied for up to one minute.

4. The method of claim 1 wherein the substrate is cellophane, cotton, rayon, wood, nylon, polyester, polyethylene glycol, adipate, cellulose triacetate, polyethylene, natural and synthetic rubbers, leather, wool, hair or skin.

5. The method according to claim 4 wherein the curing is effecting by microwave energy applied for a time period of 2-5 minutes.

6. The method of claim 4, wherein the curing is effecting by laser energy applied for up to one minute.

7. Method according to claim 1 wherein the substrate is cellophane.

8. Method according to claim 2 wherein the substrate is cellophane.

9. Method according to claim 3 wherein the substrate is cellophane.

* * * * *